(12) United States Patent
Rademacher et al.

(10) Patent No.: US 12,409,215 B2
(45) Date of Patent: Sep. 9, 2025

(54) VACCINE COMPOSITIONS

(71) Applicant: Emergex Vaccines Holding Limited, Oxfordshire (GB)

(72) Inventors: Laurens Rademacher, Oxfordshire (GB); Thomas Rademacher, Oxfordshire (GB); Ramila Philip, Sparks, NV (US)

(73) Assignee: EMERGEX VACCINES HOLDING LIMITED, Oxfordshire (GB)

( * ) Notice: Subject to any disclaimer, the term of this patent is extended or adjusted under 35 U.S.C. 154(b) by 817 days.

(21) Appl. No.: 16/982,039

(22) PCT Filed: Mar. 29, 2019

(86) PCT No.: PCT/GB2019/050928
§ 371 (c)(1),
(2) Date: Sep. 17, 2020

(87) PCT Pub. No.: WO2019/186199
PCT Pub. Date: Oct. 3, 2019

(65) Prior Publication Data
US 2021/0093708 A1    Apr. 1, 2021

Related U.S. Application Data

(60) Provisional application No. 62/649,804, filed on Mar. 29, 2018.

(51) Int. Cl.
*A61K 39/12* (2006.01)
*A61K 39/00* (2006.01)
*A61P 31/14* (2006.01)

(52) U.S. Cl.
CPC .............. *A61K 39/12* (2013.01); *A61P 31/14* (2018.01); *A61K 2039/55555* (2013.01); *A61K 2039/572* (2013.01); *A61K 2039/70* (2013.01); *C12N 2770/24134* (2013.01)

(58) Field of Classification Search
CPC .......... A61K 39/12; A61K 2039/55555; A61K 2039/572; A61K 2039/70; A61K 2039/55566; A61P 31/14; C12N 2770/24134; Y02A 50/30
See application file for complete search history.

(56) References Cited

U.S. PATENT DOCUMENTS

| | | | |
|---|---|---|---|
| 2009/0297614 A1* | 12/2009 | Rademacher | A61K 39/385 424/490 |
| 2017/0014502 A1* | 1/2017 | Sumathy | A61K 39/12 |
| 2019/0359694 A1* | 11/2019 | Lipkin | C07K 16/06 |
| 2020/0268871 A1* | 8/2020 | Philip | A61K 9/5115 |
| 2021/0361760 A1* | 11/2021 | Philip | A61K 47/6929 |

FOREIGN PATENT DOCUMENTS

| | | | |
|---|---|---|---|
| WO | 0232404 A2 | 4/2002 | |
| WO | 2006/037979 A2 | 4/2006 | |
| WO | 2007/015105 A2 | 2/2007 | |
| WO | 2007/122388 A2 | 11/2007 | |
| WO | 2013/034726 A1 | 3/2013 | |
| WO | 2015175361 A1 | 11/2015 | |
| WO | WO-2017140905 A1 * | 8/2017 | ............. A61K 39/12 |
| WO | WO-2018218355 A1 * | 12/2018 | ............ A61K 31/167 |
| WO | 2019/058133 A2 | 3/2019 | |
| WO | WO 2019/058133 | 3/2019 | |
| WO | WO 2019/135086 | 7/2019 | |

OTHER PUBLICATIONS

Santiago GA, et. a. Polyprotein [Zika virus]. GenBank: QOU08411. 1. Dep. Nov. 3, 2020. (Year: 2020).*
Nunes MRT, et al. Polyprotein [Zika virus]. GenBank: ALL27019.1. Dep. Oct. 29, 2016. (Year: 2016).*
Huang X, Karabudak A, Comber JD, Philip M, Morcol T, Philip R. A novel immunization approach for dengue infection based on conserved T cell epitopes formulated in calcium phosphate nanoparticles. Hum Vaccin Immunother. Nov. 2, 2017;13(11):2612-2625. Epub Sep. 21, 2017. (Year: 2017).*
Comber et al., "Dengue virus specific dual HLA binding T cell epitopes induce CD8+ T cell responses in seropositive individuals", *Hum Vaccin Immunother.*, 10(12):3531-3543, 2014.
Search Report and Written Opinion issued by the Intellectual Property Office of Singapore in corresponding Application No. 11202009147U dated Apr. 5, 2022.
Wen et al., "Identification of Zika virus epitopes reveals immunodominant and protective roles for dengue virus cross-reactive CD8+ T cells", *Nat Micrbiol.*, 2:17036, 2017.
Wen et al: "Identification of Zika virus epitopes reveals immunodominant and protective roles for dengue virus cross-reactive CD8+ T cells", Nature Microbiology, vol. 2, Mar. 13, 2017 (Mar. 13, 2017). p. 17036.
Comber et al: "Dengue virus specific dual HLA binding T cell epitopes induce CDS(+) T cell responses in seropositive individuals", Human Vaccines and Immunotherapeutics, Taylor & Francis, US, vol. 10, No. 12, Dec. 2, 2014 (Dec. 2, 2014), pp. 3531-3543.
Testa et al: "Role of T-cell epitope-based vaccine in prophylactic and therapeutic applications", Future Virology, vol. 7, No. 11, Nov. 1, 2012 (Nov. 1, 2012), pp. 1077-1088.
Meziere et al., (1997) J. Immunol. 159, 3230-3237.
Testa et al., "Conserved MHC class I-presented dengue virus epitopes identified by immunoproteomics analysis are targets for cross-serotype reactive T-cell response". J Infect Dis, Feb. 15, 2012, vol. 205(4), pp. 647-655.

* cited by examiner

*Primary Examiner* — Rachel B Gill
(74) *Attorney, Agent, or Firm* — NORTON ROSE FULBRIGHT US LLP

(57) ABSTRACT

The invention provides a vaccine composition comprising a flavivirus peptide comprising one or more CD8+ T cell epitopes, wherein the peptide is attached to a nanoparticle.

18 Claims, 4 Drawing Sheets
Specification includes a Sequence Listing.

VACCINE COMPOSITIONS

CROSS-REFERENCE TO RELATED APPLICATIONS

This application is a national phase application under 35 U.S.C. § 371 that claims priority to International Application No. PCT/GB2019/050928, filed Mar. 29, 2019, which claims priority to U.S. Provisional Patent Application Ser. No. 62/649,804, filed Mar. 29, 2018, both of which are incorporated by reference herein in their entirety.

SEQUENCE LISTING

The instant application contains a Sequence Listing which has been submitted electronically in ASCII format and is hereby incorporated by reference in its entirety. Said ASCII copy, created on Sep. 17, 2020, is named SL_KEMP_P0104US.txt and is 2,674 bytes in size.

STATEMENT OF COMMON OWNERSHIP

Pursuant to 35 USC § 102 (b) (2) (C) and MPEP § 2146.02 (I), Applicant hereby states that this application and U.S. patent application Ser. No. 16/644,123, not later than the effective filing date of this application, were owned by or subject to an obligation of assignment to the same person (Emergex Vaccines Holding Limited).

FIELD OF THE INVENTION

The invention relates to vaccine compositions comprising flavivirus peptides, and the use of such compositions for the treatment and prevention of flavivirus infection.

BACKGROUND TO THE INVENTION

Flaviviruses are a family of positive sense, single stranded, enveloped RNA viruses that may infect humans and pose a significant threat to public health. In particular, flaviviruses are the causative agent of Zika fever, Dengue fever, yellow fever and West Nile fever. These diseases are commonly characterised by symptoms that include fever, vomiting, headache, joint pain and muscle pain, though each disease may also be associated with more serious symptoms. For instance, mother-to-child transmission of Zika virus during pregnancy can cause brain malformations, and Zika virus infection has also been linked to Guillain-Barré syndrome. Dengue fever may progress into life-threatening Dengue haemorrhagic syndrome or Dengue shock syndrome. Yellow fever may induce liver damage, which may result in bleeding and kidney problems. West Nile fever may spread to the nervous system, causing encephalitis or meningitis.

Flaviviruses are arboviruses, meaning that they are transmitted by infected arthropod vectors such as mosquitos and ticks. The geographical distribution of flaviviruses is primarily determined by that of their arthropod vector. For the most part, the vectors are confined to tropical and subtropical regions, such as Southeast Asia and South America. However, climate change appears to be broadening the distribution of some vectors, thereby increasing the population at risk of contracting flavivirus infections. Furthermore, the mosquito responsible for spreading Zika virus and yellow fever virus has been shown to be able to adapt to survive in high-density urban areas. It is therefore important to find effective methods for containing flavivirus infection.

While some flaviviruses (such as West Nile virus) only incidentally infect humans, other flaviviruses (such as yellow fever virus, Dengue virus and Zika virus) exist predominantly in an arthropod-human life cycle. Such flaviviruses grow well in the human host, and high viral titres allow infection to cycle back to arthropod vectors and onto new human hosts. In either case, vector-born transmission and the ability to infect other species such as monkeys and birds means that flavivirus infection tend to spread quickly and easily. Controlling the spread of flavivirus infections is therefore challenging.

The structure of the flavivirus genome also contributes to the challenge of controlling spread. Few proof-reading and correction mechanisms exist for the replication of single-stranded RNA. Therefore, mutations arising in the course of replication frequently remain in the genome and are passed to the next generation. Flaviviruses therefore evolve quickly.

While a safe and effective vaccine exists for yellow fever infection, this is not the case for Zika virus, Dengue virus or West Nile virus infection. A vaccine for Dengue virus exists, but is recommended only for use in individuals who have previously had a Dengue virus infection, as outcomes may be worsened in those who have not previously been infected. Being exposed to one serotype of Dengue virus (such as DENV-1, DENV-2, DENV-3 or DENV-4) potentially worsens subsequent infections with another Dengue serotype, and so Dengue vaccine currently in trial include included Dengue serotypes in their formulations. As Zika virus is closely related to Dengue virus, any Zika virus vaccine also needs to minimize the possibility of antibody-dependent enhancement of Dengue virus infection. There is therefore a need for effective vaccines against Zika virus, Dengue virus and West Nile virus infection.

SUMMARY OF THE INVENTION

The present invention relates to a flavivirus vaccine composition that stimulates an immune response while avoiding the adverse clinical effects often associated with vaccines containing viruses. The vaccine composition may provide protection against multiple species of flavivirus (e.g. Zika virus, Dengue virus and/or West Nile virus) and/or multiple lineages or serotypes of a particular species (e.g. African Zika virus, Asian Zika virus, DENV-1, DENV-2, DENV-3 and/or DENV-4).

The present inventors have surprisingly identified that a nanoparticle, for example a gold nanoparticle, may be used to induce an efficient response to a vaccine composition designed to stimulate a T cell response against a flavivirus. Use of a nanoparticle abrogates the need to use a virus in the vaccine composition. The use of a traditional adjuvant, which may be associated with adverse reactions in the clinic, is also avoided. Therefore, the likelihood of an individual experiencing an adverse reaction following administration of the vaccine composition is reduced.

The present inventors have also identified number of peptides that are conserved between different flaviviruses and are presented by MHC molecules on cells infected with those viruses. Inclusion of such conserved peptides in the vaccine composition may confer protective capability against multiple species of flavivirus and/or multiple lineages or serotypes of a particular species. Including multiple conserved peptides that bind to different HLA supertypes in the vaccine composition results in a vaccine that is effective in individuals having different HLA types.

Accordingly, the present invention provides a vaccine composition comprising a flavivirus peptide comprising one or more of the CD8+ T cell epitopes set out in SEQ ID NOs: 1 to 10. In some aspects, the flavivirus peptide may be attached to a nanoparticle.

The present invention further provides:
- a method of preventing or treating a flavivirus infection, comprising administering the vaccine composition of any one of the preceding claims to an individual infected with, or at risk of being infected with, a flavivirus; and
- a vaccine composition of the invention for use in a method of preventing or treating a flavivirus infection in an individual.

BRIEF DESCRIPTION OF THE FIGURES

FIG. 5 shows that HepG2 target cells contain peptide class I targets that are able to simulate spleen cells from transgenic A2 mice. Acid stripping of the peptides makes the cells non-response.

FIG. 6 shows that spleen cells from unimmunized mice do not respond to dengue or zika infected cells. In contrast A2 mice immunized with NP-Dengue or NP-Zika peptides are able to kill both Dengue or Zika infected HepG2 cells.

DETAILED DESCRIPTION OF THE INVENTION

Vaccine Compositions

Figure 1:
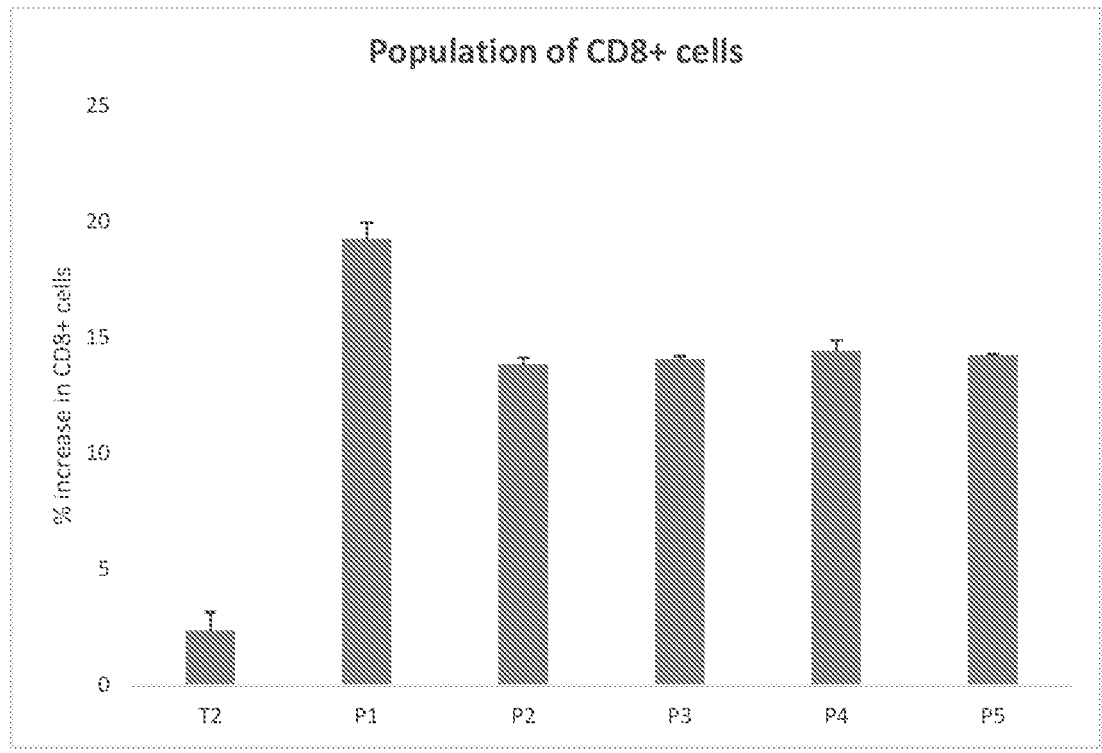
FIG. 1: Activated PBMCs were analysed for levels of CD8 to determine expansion of this population of cells. All 5 peptides caused (P1-5) cell expansion. Non-loaded T2 cells (T2) acted as control. The error bars represent the standard deviation of the replicates.
Figure 2:
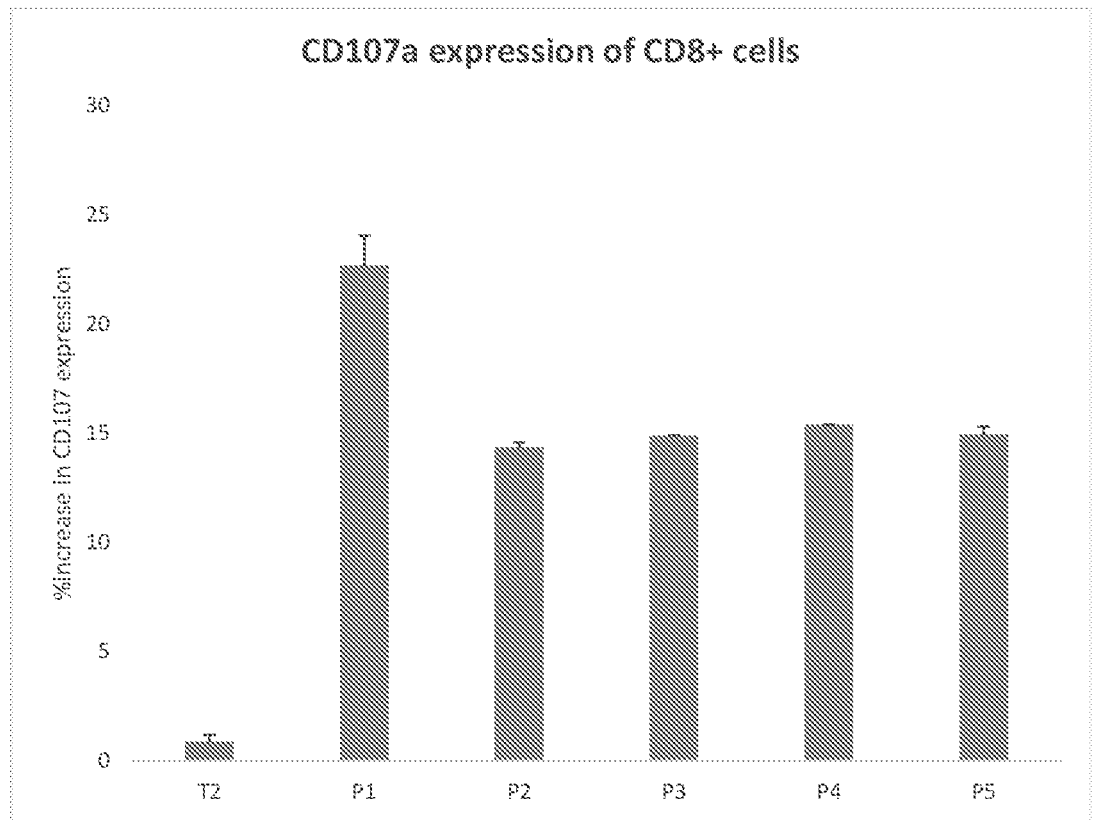
FIG. 2: The CD107a expression from CD8+ population of PBMCs after activation with peptide loaded T2s. All 5 peptide (P1-5) epitopes activated CD8+ T cells to respond to peptide loaded T2 cells in a Flavivirus peptide specific manner. The error bars represent the standard deviation of the replicates peptide specific manner. Non-loaded T2 cells (T2) acted as control.
Figure 3:
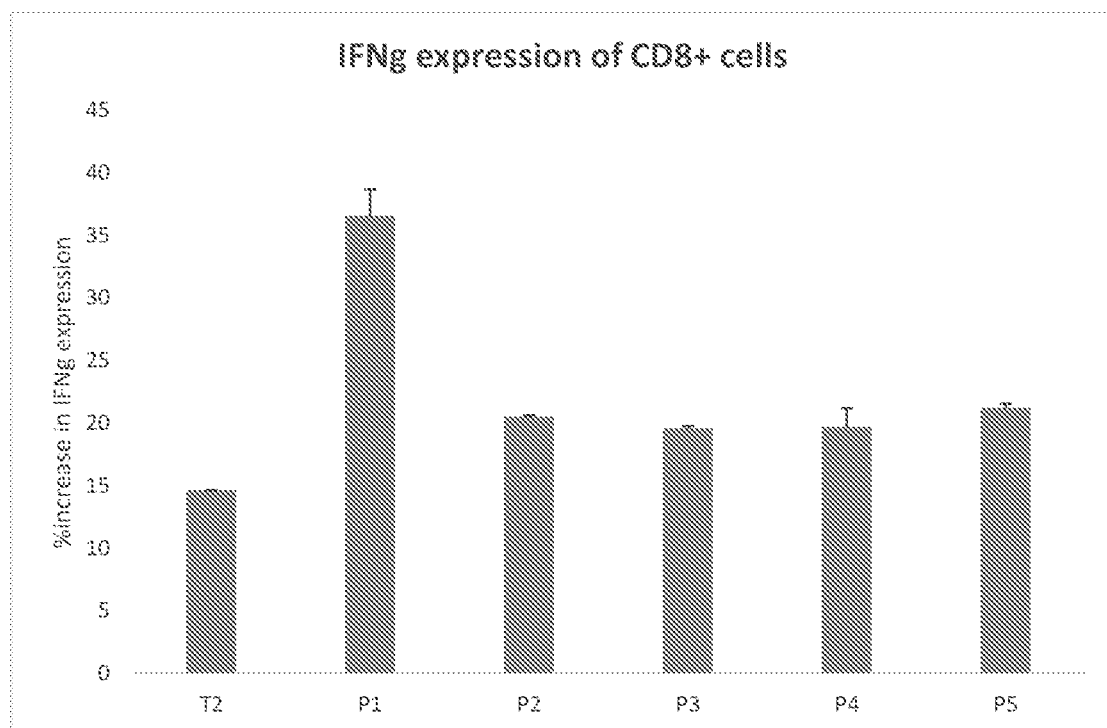
FIG. 3: The IFNγ expression from CD8+ population of PBMCs after activation with peptide loaded T2s. All 5 peptide (P1-5) epitopes activated CD8+ T cells to respond to peptide loaded T2 cells in a Flavivirus peptide specific manner. Non-loaded T2 cells (T2) acted as control. The error bars represent the standard deviation of the replicates.
Figure 4:
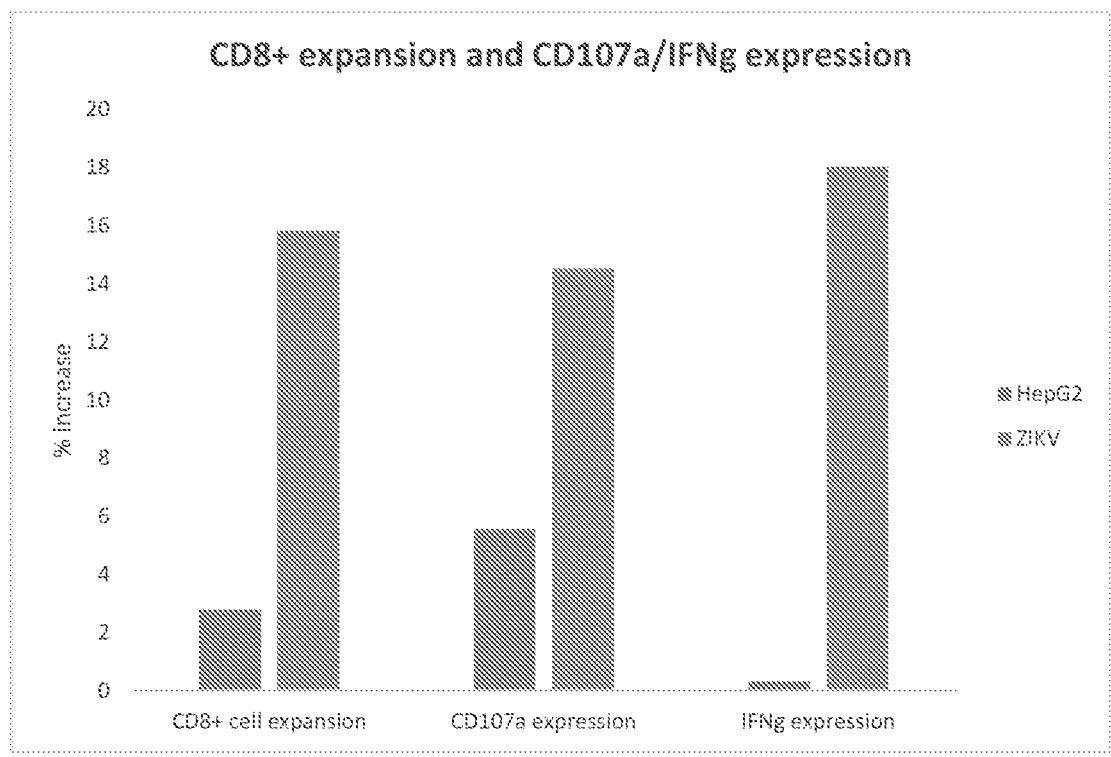
FIG. 4: The ability of PMBCs stimulated with pooled Zika peptides (P1-P5) to kill Zika infected cells was investigated. PBMCs were stimulated were activated with peptide loaded T2. The response (CD8+ T cell expansion, CD107a expression, IFNγ expression) of stimulated PBMCs to uninfected HepG2 cells (HepG2; control) or HepG2 cells infected with Zika virus (ZIKV) was measured. Zika peptide stimulated PMBCs exposed to healthy HepG2 cells show around 3% CD8+ cell expansion, whereas Zika peptide stimulated PMBCs exposed to zika infected HepG2 cells show around 16% expansion CD8+ cell. CD107a expression and IFNγ expression is markedly greater for Zika peptide stimulated PMBCs exposed to zika infected HepG2 cells than for Zika peptide stimulated PMBCs exposed to uninfected HepG2 cells. This suggests that the PMBCs "recognise" the Zika infected cells.

The present invention provides a vaccine composition comprising a flavivirus peptide comprising one or more of the CD8+ T cell epitopes set out in SEQ ID NOs: 1 to 10. This vaccine composition has a number of benefits which will become apparent from the discussion below. The key benefits are though summarised here.

Firstly, the vaccine composition of the invention advantageously comprises a flavivirus peptide comprising one or more of the CD8+ T cell epitopes set out in SEQ ID NOs: 1 to 10 and newly identified by the inventors. As demonstrated in the Examples, the vaccine composition is therefore capable of stimulating a cellular immune response (e.g. a CD8+ T cell response) against a flavivirus. CD8+ cytotoxic T lymphocytes (CTLs) mediate viral clearance via their cytotoxic activity against infected cells. Stimulating cellular immunity may therefore provide a beneficial defence against flavivirus infection.

Secondly, a number of the CD8+ T cell epitopes identified by the present inventors may be conserved between many different flaviviruses, and may be presented by MHC molecules on cells infected with those viruses. For instance, the present inventors have identified that certain CD8+ T cell epitopes expressed in cells infected with Zika virus are 100% homologous with peptides expressed by other flaviviruses, such as Dengue virus and/or West Nile virus (see Tables 1 and 2). Inclusion of such conserved peptides in the vaccine composition may confer protective capability against multiple species of flavivirus and/or multiple lineages or serotypes of a particular species, i.e. confer cross-protection. 100% homology between flaviviruses is not required for cross-protection to be conferred. Rather, cross-protection may arise following immunisation with a sequence that is, for example, about 50% or more (such as 60%, 70%, 75%, 80%, 90%, 95%, 98% or 99%) homologous to a CD8+ T cell epitope expressed in a cell infected with Zika virus, if certain residues are retained in the correct position. A vaccine composition comprising one or more CD8+ T cell epitopes set out in SEQ ID NOs: 1 to 10 may therefore be capable of providing cross-protection against a wide variety of existing flaviviruses over and above those recited in Table 1 and 2. Inclusion of one or more conserved peptides in the vaccine composition may also confer protective capability against emerging flavivirus strains associated with rapid evolution of the flavivirus genome. In this way, a single flavivirus vaccine composition can be used to confer protection against a variety of different flaviviruses. This provides a cost-effective means of controlling the spread of flavivirus infection.

Thirdly, different CD8+ T cell epitopes identified by the present inventors are capable of binding to different HLA supertypes. Inclusion of multiple peptides each comprising a CD8+ T cell epitope capable of binding to a different HLA supertypes results in a vaccine composition that is effective in individuals having different HLA types. In this way, a single flavivirus vaccine composition can be used to confer protection in a large proportion of the human population. This again provides a cost-effective means of controlling the spread of flavivirus infection.

Fourthly, the flavivirus peptide comprised in the vaccine composition of the invention may be attached to a nanoparticle, for example a gold nanoparticle. As described in more detail below, attachment to a nanoparticle reduces or eliminates the need to include an adjuvant in the vaccine composition. Thus, the vaccine composition of the invention is less likely to cause adverse clinical effects upon administration to an individual.

Peptides

The vaccine composition of the invention comprises a flavivirus peptide comprising one or more of the CD8+ T cell epitopes set out in SEQ ID NOs: 1 to 10. The vaccine composition may comprise from about one to about 50 such peptides, such as about 2 to 40, 3 to 30, 4 to 25, 5 to 20, 6 to 15, 7, 8, 9 or 10 such peptides. SEQ ID NOs: 1 to 10 are set out in Table 1.

TABLE 1

| SEQ ID NO: | Sequence | Protein ID | HLA affinity | Origin | 100% sequence homology with . . . |
|---|---|---|---|---|---|
| 1 | PMAAVGLLIVS | NS2B | A2/A24 | Zika infected cells | Zika virus |
| 2 | AILEENGVQ | NS4B | A2 | Zika infected cells | Zika virus |
| 3 | SPRRLAAAV | NS1 | B7 | Zika infected cells | Zika virus, Dengue virus |
| 4 | DPAVIGTAVK | NS1 | B7 | Zika infected cells | Zika virus |
| 5 | WVTDHSGKTV | NS3 | A2 | Dengue infected cells | Zika virus, West Nile virus, Dengue virus |
| 6 | PFGDSYIVIGVGE | Envelope | A24 | Zika infected cells | Zika virus, |
| 7 | DIGAVALDYPA | NS3 | A24 | Zika infected cells | DENV- 4 |
| 8 | LLGLITANEL | Peptike 2k | A2/A24 | Zika infected cells | Zika virus |
| 9 | IMLLGLLGTV | NS4 | A2 | Zika infected cells | Zika virus |
| 10 | LMRNKGIGK | NS4A | A3 | Dengue infected cells | Zika virus |

The flavivirus peptide comprising one or more of the CD8+ T cell epitopes set out in SEQ ID NOs: 1 to 10 may comprise only one of the CD8+ T cell epitopes set out in SEQ ID NOs: 1 to 10. Alternatively, the flavivirus peptide comprising one or more of the CD8+ T cell epitopes set out in SEQ ID NOs: 1 to 10 may comprise two or more, such as three or more, four or more, five or more, six or more, seven or more, eight or more, or nine or more of the CD8+ T cell epitopes set out in SEQ ID NOs: 1 to 10, in any combination. The flavivirus peptide comprising one or more of the CD8+ T cell epitopes set out in SEQ ID NOs: 1 to 10 may comprise all of the CD8+ T cell epitopes set out in SEQ ID NOs: 1 to 10.

As well as one or more of the CD8+ T cell epitopes set out in SEQ ID NOs: 1 to 10, the flavivirus peptide may comprise one or more other CD8+ T cell epitopes, one or more CD4+ T cell epitopes and/or one or more B cell epitopes. For example, the flavivirus peptide may comprise two or more, such as three or more, four or more, five or more, ten or more, fifteen or more, or twenty or more CD8+ T cell epitopes other than those set out in SEQ ID NOs: 1 to 10.

The flavivirus peptide may comprise two or more, such as three or more, four or more, five or more, ten or more, fifteen or more, or twenty or more CD4+ T cell epitopes. The flavivirus peptide may comprise two or more, such as three or more, four or more, five or more, ten or more, fifteen or more, or twenty or more B cell epitopes.

The vaccine composition may comprise two or more flavivirus peptides each comprising a CD8+ T cell epitope comprising a different sequence selected from SEQ ID NOs: 1 to 10. Each of the flavivirus peptides may have any of the properties set out in the preceding paragraphs. For instance, each flavivirus peptide may comprise multiple CD8+ T cell epitopes set out in SEQ ID NOs: 1 to 10 and, optionally, one or more other CD8+ T cell epitopes, one or more CD4+ T cell epitopes and/or one or more B cell epitopes. In one aspect, the vaccine composition may comprise three or more, four or more, five or more, six or more, seven or more, eight or more, or nine or more flavivirus peptides each comprising a CD8+ T cell epitope comprising a different sequence selected from SEQ ID NOs: 1 to 10. The vaccine composition may, for example, comprise 10 flavivirus peptides each comprising a CD8+ T cell epitope comprising a different sequence selected from SEQ ID NOs: 1 to 10.

The vaccine composition may further comprise one or more (such as about 1 to 50, 2 to 40, 3 to 30, 4 to 25, 5 to 20, 6 to 15, 7, 8, 10 or 10) additional peptides each comprising one or more epitopes. The epitope may be a CD8+ T cell epitope, a CD4+ T cell epitope and/or a B cell epitope. The CD8+ T cell epitope is preferably a CD8+ T cell epitope other than the CD8+ T cell epitopes set out in SEQ ID NOs: 1 to 10. The CD8+ T cell epitope may, for example, be a flavivirus CD8+ epitope, i.e. a peptide that is expressed by one or more flaviviruses and that is that is capable of (i) presentation by a class I MHC molecule and (ii) recognition by a T cell receptor (TCR) present on a CD8+ T cell.

Alternatively, the CD8+ T cell epitope may be an CD8+ T cell epitope that is not expressed by one or more flaviviruses. The CD4+ T cell epitope may, for example, be a flavivirus CD4+ epitope, i.e. a peptide that is expressed by one or more flaviviruses and that is that is capable of (i) presentation by a class II MHC molecule and (ii) recognition by a T cell receptor (TCR) present on a CD4+ T cell. Alternatively, the CD4+ T cell epitope may be an CD4+ T cell epitope that is not expressed by one or more flaviviruses. CD8+ and CD4+ T cell epitopes are described in more detail below.

A flavivirus peptide is a peptide that is expressed by one or more flaviviruses. Numerous species of flavivirus exist, including Zika virus, Dengue virus, West Nile virus and yellow fever virus, as well as St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus. There are four serotypes of Dengue virus (DENV-1, DENV-2, DENV-3 and DENV-4) and two strains of Zika virus (African Zika virus and Asian Zika virus).

Any flavivirus peptide comprised in the vaccine composition of the invention may comprise a peptide that is expressed by one or more of Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus. For example, a flavivirus peptide comprised in the vaccine composition of the invention may comprise a peptide that is expressed by Zika virus and Dengue virus, or Zika virus, Dengue virus and West Nile virus. For instance, the flavuvirus peptide comprising one or more of the CD8+ T cell epitopes set out in SEQ ID NOs: 1 to 10 may be expressed by (i) one or more of Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest virus, Omsk Hemorrhagic Fever virus, Powassan virus, Louping Ill virus, Rio Bravo virus, Tyuleniy virus, Ntaya virus and Modoc virus; (ii) Zika virus and Dengue virus; or (iii) Zika virus, Dengue virus and West Nile virus. Likewise, when the composition comprises an additional peptide that is a flavivirus peptide, that additional filovirus peptide may be expressed by (i) one or more of Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest, Omsk Hemorrhagic Fever virus, Powassan virus, Louping Ill virus, Rio Bravo virus, Tyuleniy virus, Ntaya virus and Modoc virus; (ii) Zika virus and Dengue virus; or (iii) Zika virus, Dengue virus and West Nile virus. Accordingly, the vaccine composition may comprise flavivirus peptides from one or more species of flavivirus, such as 1 to 20, 2 to 19, 3 to 18, 4 to 17, 5 to 16, 6 to 15, 7 to 14, 8 to 13, 9 to 12, 10 or 11 species of flaviviruses.

When a flavivirus peptide comprised in the vaccine composition of the invention comprises a peptide that is expressed by Zika virus, the peptide may be expressed by African Zika virus, Asian Zika virus, or both African Zika virus and Asian Zika virus. When a flavivirus peptide comprised in the vaccine composition of the invention comprises a peptide that is expressed by Dengue virus, the peptide may be expressed by one or more of DENV-1, DENV-2, DENV-3 and DENV-4 in any combination such as, for example: 1; 2; 3; 4; 1 and 2; 1 and 3; 1 and 4; 2 and 3; 2 and 4; 3 and 4; 1, 2 and 3; 1, 2 and 4; 1, 3 and 4; 2, 3 and 4; or 1, 2, 3 and 4.

The flavivirus peptide may be a peptide that is expressed on the surface of one or more flaviviruses, or intracellularly within one or more flaviviruses. The peptide may be a structural peptide or a functional peptide, such as a peptide involved in the metabolism or replication of the flavivirus. Preferably, the peptide is an internal peptide. Preferably, the peptide is conserved between two or more different flaviviruses or flavivirus serotypes. A peptide is conserved between two or more different flaviviruses or flavivirus serotypes if each of the two or more different flaviviruses or flavivirus serotypes encodes a sequence that is 50% or more (such as 60%, 70%, 75%, 80%, 90%, 95%, 98% or 99%) homologous to the peptide.

The flavivirus peptide may contain any number of amino acids, i.e. be of any length. Typically, the flavivirus peptide is about 8 to about 30, 35 or 40 amino acids in length, such as about 9 to about 29, about 10 to about 28, about 11 to about 27, about 12 to about 26, about 13 to about 25, about 13 to about 24, about 14 to about 23, about 15 to about 22, about 16 to about 21, about 17 to about 20, or about 18 to about 29 amino acids in length.

The flavivirus peptide may be chemically derived from a polypeptide flavivirus antigen, for example by proteolytic cleavage. More typically, the flavivirus peptide may be synthesised using methods well known in the art.

The term "peptide" includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al (1997) J. Immunol. 159, 3230-3237. This approach involves making pseudopeptides containing changes involving the backbone, and not the orientation of side chains. Meziere et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond. It will also be appreciated that the peptide may conveniently be blocked at its N- or C-terminus so as to help reduce susceptibility to exoproteolytic digestion. For example, the N-terminal amino group of the peptides may be protected by reacting with a carboxylic acid and the C-terminal carboxyl group of the peptide may be protected by reacting with an amine. Other examples of modifications include glycosylation and phosphorylation. Another potential modification is that hydrogens on the side chain amines of R or K may be replaced with methylene groups (—NH2 may be modified to —NH(Me) or —N(Me)$_2$).

The term "peptide" also includes peptide variants that increase or decrease the half-life of the peptide in vivo.

Examples of analogues capable of increasing the half-life of peptides used according to the invention include peptoid analogues of the peptides, D-amino acid derivatives of the peptides, and peptide-peptoid hybrids. A further embodiment of the variant polypeptides used according to the invention comprises D-amino acid forms of the polypeptide. The preparation of polypeptides using D-amino acids rather than L-amino acids greatly decreases any unwanted breakdown of such an agent by normal metabolic processes, decreasing the amounts of agent which needs to be administered, along with the frequency of its administration.

CD8+ T Cell Epitopes

The vaccine composition of the invention comprises a flavivirus peptide comprising one or more of the CD8+ T cell epitopes set out in SEQ ID NOs: 1 to 10 (see Table 1). The flavivirus peptide comprising one or more of the CD8+ T cell epitopes set out in SEQ ID NOs: 1 to 10 may further comprise one or more (such as two or more, three or more, four or more, five or more, ten or more, fifteen or more, or twenty or more) other CD8+ T cell epitopes. The vaccine composition may further comprise one or more (such as 1 to 50, 2 to 40, 3 to 30, 4 to 25, 5 to 20, 6 to 15, 7, 8, 9 or 10) additional peptides each comprising one or more CD8+ T cell epitopes. Preferably, the additional peptide is a flavivirus peptide.

A CD8+ T cell epitope is a peptide that is capable of (i) presentation by a class I MHC molecule and (ii) recognition by a T cell receptor (TCR) present on a CD8+ T cell. Preferably, recognition by the TCR results in activation of the CD8+ T cell. CD8+ T cell activation may lead to increased proliferation, cytokine production and/or cyotoxic effects.

Typically, the CD8+ T cell epitope is around 9 amino acids in length. The CD8+ T cell epitope may though be shorter or longer. For example, the CD8+ T cell epitope may be about 8, 9, 10, 11, 12, 13, 14 or 15 amino acids in length. The CD8+ T cell epitope may be about 8 to 15, 9 to 14 or 10 to 12 amino acids in length.

Flavivirus peptides comprising a CD8+ T cell epitope are known in the art. Methods for identifying CD8+ T cell epitopes are known in the art. Epitope mapping methods include X-ray co-crystallography, array-based oligo-peptide scanning (sometimes called overlapping peptide scan or pepscan analysis), site-directed mutagenesis, high throughput mutagenesis mapping, hydrogen-deuterium exchange, crosslinking coupled mass spectrometry, phage display and limited proteolysis. MHC motif prediction methodologies may also be used.

CD8+ T cell epitopes presented by flavivirus-infected cells can be identified in order to directly identify CD8+ T cell epitopes for inclusion in the vaccine composition. This is an efficient and logical method which can be used alone or to confirm the utility of potential CD8+ T cell epitopes identified by MHC motif prediction methodologies. This method was used by the inventors to identify the CD8+ T cell epitopes set out in SEQ ID NOs: 1 to 10 (see Example 1).

To perform the method, cells are infected with a flavivirus and maintained in culture for a period of around 72 hours at a temperature of around 37° C. Following culture, the cells are then harvested and washed. Next, the cells are lysed, for instance by homogenisation and freezing/thawing in buffer containing 1% NP40. Lysates are cleared by centrifugation at 2000 rpm for 30 minutes to remove cell debris.

MHC/peptide complexes are then isolated from the lysates by immunoaffinity chromatography using protein A/G beads (UltraLink Immobilized Protein A/G, pierce, Rockford, IL) coated with W6/32 (a monoclonal antibody recognising pan MHC class I molecule). To coat the beads with the antibody, the beads are washed with low pH buffer followed by PBS rinses, incubated with 0.5 mg of the antibody at room temperature for 2 hours, and washed three times to remove unbound antibody. For immunoaffinity chromatography, the coated beads are incubate with lysate for 2 hours at room temperature with continuous rocking. The beads are then separated from the lysate by centrifuging at 1000 rpm for 5 minutes. Bound MHC complexes are eluted from the beads by the addition of 0.1% trifluoroacetic acid (TFA), pH 1.5.

The eluate is next heated at 85° C. for 15 minutes to dissociate the bound peptides from the MHC molecules. After cooling to room temperature, peptides are separated from the antibody by centrifugation using, for example, 3 kDa molecular mass cutoff membrane filters (Millipore). The filtrate is concentrated using vacuum centrifugation and reconstituted to a final volume of 100 µl. The purified peptide mixture is fractionated, for example using a C-18 reversed phase (RP) column (e.g. 4.6 mm diameter×150 mm length) using an offline HPLC. For this step, mobile phase A may be 2% acetonitrile (CAN) and 0.1% formic acid (FA) in water, while mobile phase B may be 0.1% FA and 90% CAN in water.

The peptide-containing fractions are then eluted from the column, dried under a vacuum, and analysed by mass spectrometry to identify the sequences of the fractions. The acquired spectral data can then be searched against all databased flavivirus proteins to identify peptide sequences associated with flavivirus. Synthetic peptides may then be made according to the identified sequences and subjected to mass spectrometry to confirm their identity to the peptides in the peptide-containing fractions.

In this method, any type of cells may be infected with flavivirus. The cells may be antigen presenting cells. The cells may be hepatoma cells such as HepG2 cells, EBV-transformed lymphoblastoid B cells such as JY cells, or lymphoblasts such as T2 cells.

Likewise, any flavivirus of interest may be used to infect the cells. For instance, the flavivirus may be Zika virus, Dengue virus, West Nile virus, yellow fever virus, St. Louis encephalitis virus, Japanese encephalitis virus, Murray Valley encephalitis virus, Tick-borne encephalitis virus, Kunjin encephalitis virus, Rocio encephalitis virus, Russian Spring Summer encephalitis virus, Negeishi virus, Kyasanur Forest, Omsk Hemorrhagic Fever virus, Powassan virus, Louping Ill virus, Rio Bravo virus, Tyuleniy virus, Ntaya virus and Modoc virus. The Zika virus may, for example, be African Zika Virus or Asian Zika Virus. The Dengue virus may, for example, be DENV-1, DENV-2, DENV-3 or DENV-4.

The direct identification of CD8+ T cell epitopes presented by flavivirus-infected cells is advantageous compared to MHC motif prediction methodologies. The immune epitope database (IEDB; http://www.iedb.org) is generated by motif prediction methods, and not functional methods, and contains numerous predicted HLA-specific flavivirus T cell epitopes, including some shared epitopes with high MHC binding scores and limited CTL characterization. As both dominant and subdominant epitopes may be presented by flavivirus-infected cells, it is difficult to sort out the dominance hierarchies of naturally presented epitopes using the database. Thus, it is not clear from the immune epitope database alone which of the listed epitopes may be expected to efficiently induce a CD8+ T cell response when included in a vaccine composition. The direct identification method set out above provides a mechanism for confirming the utility of the epitopes.

Vaccine compositions based on epitopes presented by flavivirus-infected cells, such as the vaccine composition of the invention, are superior to vaccines based on a viral protein subunit or a motif predicted epitope. Protein processing by the immune system is likely to alter native viral epitopes. Basing a vaccine composition on peptides demonstrated to be presented by infected cells removes this source of uncertainty, because the peptides have already undergone protein processing.

Furthermore, the direct identification method may be used to identify conserved CD8+ T cell epitopes presented by cells infected by different flaviviruses. In this way, CD8+ T cell epitopes suitable for inclusion in a cross-protective vaccine may be identified. As set out in the Examples, the present inventors confirmed that the peptides SPRRLAAAV (SEQ ID NO: 3) and PFGDSYIVIGVGE (SEQ ID NO: 6), are Zika virus CD8+ T cell epitopes having 100% homology with sequences encoded by Dengue virus, and that WVTDHSGKTV (SEQ ID NO: 5) is a Dengue virus CD8+ T cell epitope having 100% homology with sequences encoded by Zika virus and West Nile virus.

Cross Protective Vaccine Compositions

Each of SEQ ID NOs: 1 to 10 identified by the present inventors is either (i) derived from Zika virus infected cells, or (ii) derived from Dengue virus infected cells but 100% homologous with a sequence encoded by Zika virus. The vaccine composition of the invention is therefore designed to elicit a protective immune response against Zika virus infection. However, the vaccine composition may also induce cross-protection against a wide range of other flaviviruses, as the SEQ ID NOs: 1 to 10 are highly conserved between flaviviruses.

As shown in Table 1, many of the CD8+ T cell epitopes set out in SEQ ID NOs: 1 to 10 have 100% homology with a sequence encoded by a flavivirus other than that in which the epitope was initially identified. For instance, SPRRLAAAV (SEQ ID NO: 3) and PFGDSYIVIGVGE (SEQ ID NO: 6) were identified in Zika virus infected cells, but are each 100% homologous to a sequence encoded by Dengue virus. WVTDHSGKTV (SEQ ID NO: 5) was identified in Dengue virus infected cells but has 100% homology with a sequence encoded by Zika virus and a sequence encoded by West Nile virus. An immune response generated by vaccination with a composition that comprises an epitope that is 100% homologous with a sequence from another flavivirus may protect against subsequent infection with that flavivirus.

An immune response generated by vaccination with a composition that comprises an epitope that is about 50% or more (such as 60%, 70%, 75%, 80%, 90%, 95%, 98% or 99%) homologous with a sequence encoded by another flavivirus may protect against subsequent infection with that flavivirus. In some cases, the protective effect is associated with the conservation of certain residues between the epitope and the sequence encoded by the other flavivirus. Immunisation with a vaccine composition of the invention may therefore induce a protective immune response against a wide variety of flaviviruses not mentioned in Table 1 or Table 2.

Accordingly, the vaccine composition of the invention may have built-in cross-species and/or cross-genus efficacy, i.e. be a cross-protective flavivirus vaccine composition. In this way, a single flavivirus vaccine composition can be used to confer protection against a variety of different flaviviruses. This provides a cost-effective means of controlling the spread of flavivirus infection.

Inclusion of conserved peptides in the vaccine composition may confer protective capability against emerging flavivirus strains associated with rapid evolution of the flavivirus genome. This may assist in the long-term control of the flavivirus infection.

Inclusion of a flavivirus peptide comprising a conserved CD8+ T cell epitope in the vaccine composition of the invention may beneficially prevent or minimise the development of antibody-dependent enhancement of Dengue virus infection following administration of the vaccine composition.

Interaction with HLA Supertypes

The vaccine composition may comprise at least two flavivirus peptides comprising a CD8+ T cell epitope which each interacts with a different HLA supertype. Including a plurality of such peptides in the vaccine composition allows the vaccine composition to elicit a CD8+ T cell response in a greater proportion of individuals to which the vaccine composition is administered. This is because the vaccine composition should be capable of eliciting a CD8+ T cell response in all individuals of an HLA supertype that interacts with one of the CD8+ T cell epitopes comprised in the plurality of flavivirus peptides. Each CD8+ T cell epitope may interact with HLA-A1, HLA-A2, HLA-A3, HLA-A24, HLA-B7, HLA-B8, HLA-B27, HLA-B44, HLA-B58 or HLA-B62, or any other HLA supertype know in the art. Any combination of flavivirus peptides comprising such a CD8+ T cell epitope is possible.

The vaccine composition may comprise at least one flavivirus peptide comprising a CD8+ T cell epitope which interacts at least two different HLA supertypes. Again, this allows the vaccine composition to elicit a CD8+ T cell response in a greater proportion of individuals to which the vaccine composition is administered. The vaccine composition may comprise at least two, at least three, at least four, at least five, at least two, at least fifteen, or at least twenty flavivirus peptides comprising a CD8+ T cell epitope that each interact with at least two different HLA subtypes. Each flavivirus peptide may interact with at least two, at least three, at least four, at least five, at least six, at least 7, at least 8, at least 9 or at least 10 different HLA supertypes. Each flavivirus peptide may interact with two or more of HLA-A1, HLA-A2, HLA-A3, HLA-A24, HLA-B7, HLA-B8, HLA-B27, HLA-B44, HLA-B58 or HLA-B62, or any other HLA supertype known in the art, in any combination. Preferably, the vaccine composition comprises a flavivirus peptide comprising a CD8+ T cell epitope that interacts with HLA-A2 and HLA-24. In this case, the vaccine composition may, for example, comprise a filovirus peptide comprising a CD8+ T cell set out in SEQ ID NO: 1 or SEQ ID NO: 8.

CD4+ T Cell Epitopes

The vaccine composition of the invention may comprise a peptide comprising a CD4+ T cell epitope. The vaccine composition may comprise two or more, such as three or more, four or more, five our more, ten or more, fifteen or more or twenty or more peptides comprising a CD4+ T cell epitope. A CD4+ T cell epitope is a peptide that is capable of (i) presentation by a class II MHC molecule and (ii) recognition by a T cell receptor (TCR) present on a CD4+ T cell. Preferably, recognition by the TCR results in activation of the CD4+ T cell. CD4+ T cell activation may lead to increased proliferation and/or cytokine production.

The CD4+ T cell epitope may be a flavivirus CD4+ T cell epitope. That is, the CD4+ T cell epitope may be a peptide that is expressed by one or more flaviviruses and that is that is capable of (i) presentation by a class II MHC molecule and (ii) recognition by a T cell receptor (TCR) present on a CD4+ T cell. Such peptides are known in the art.

The CD4+ T cell epitope may be a CD4+ T cell epitope other than a flavivirus CD4+ T cell epitope. For example, the CD4+ T cell may be expressed by an organism other than a flavivirus. The CD4+ T cell epitope may, for example, be expressed by *Clostriudium tetani*. For instance, the CD4+ T cell epitope may be derived from tetanus toxin.

The CD4+ T cell epitope may be a CD4+ T cell epitope that reacts with all class II HLA types, i.e. a so-called "promiscuous" epitope. Inclusion of a promiscuous epitope in the vaccine composition may improve the ability of the vaccine composition to induce an immune response to the flavivirus peptide comprising one or more of the CD8+ T cell epitopes set out in SEQ ID NOs: 1 to 10. The CD4+ T cell epitope may, for example, comprise the sequence FKLQTMVKLFNRIKNNVA (SEQ ID NO: 11) and/or the sequence LQTMVKLFNRIKNNVAGGC (SEQ ID NO: 12). SEQ ID NOs 11 and 12 are promiscuous epitopes derived from tetanus toxin.

The peptide comprising a CD4+ T cell epitope may be a different peptide from the flavivirus peptide comprising one or more of the CD8+ T cell epitopes set out in SEQ ID NOs: 1 to 10. The CD4+ T cell epitope may, for instance, be comprised in an additional peptide in the vaccine composition, i.e. in a peptide that does not comprise one or more of the CD8+ T cell epitopes set out in SEQ ID NOs: 1 to 10. As mentioned above, the additional peptide may comprise one or more CD8+ T cell epitopes and/or one or more B cell epitopes as well as the CD4+ T cell epitope. For instance, the additional peptide may comprise one or more flavivirus CD8+ T cell epitopes.

The peptide comprising a CD4+ T cell epitope may be the same peptide as the flavivirus peptide comprising one or more of the CD8+ T cell epitopes set out in SEQ ID NOs: 1 to 10. That is, the flavivirus peptide comprising one or more of the CD8+ T cell epitopes set out in SEQ ID NOs: 1 to 10 may further comprise a CD4+ T cell epitope.

When the peptide comprising a CD4+ T cell epitope also comprises a CD8+ T cell epitope (such as one or more of the CD8+ T cell epitopes set out in SEQ ID NOs: 1 to 10), the CD8+ epitope may be nested within the CD4+ T cell epitope. CD4+ T cell epitopes are typically longer than CD8+ T cell epitopes. Therefore, extending one or both termini of the CD8+ T cell epitope may yield a longer, CD4+ T cell epitope whose sequence still comprises the CD8+ T cell epitope. Therefore, the CD4+ T cell epitope may comprise a CD8+ T cell epitope, such as a CD8+ T cell epitope set out in SEQ ID NOs: 1 to 10, extended at its N-terminus or C-terminus. The CD8+ T cell epitope may be extended by 1, 2, 3, 4 or 5 amino acids at its N terminus. The CD8+ T cell epitope may be extended by 1, 2, 3, 4 or 5 amino acids at its C terminus. Preferably, the CD8+ T cell epitope is extended by 3 amino acids at the N terminus, and 3 amino acids at the C terminus. However, the CD8+ T cell epitope need not be extended by the same number of amino acids at each terminus.

The CD8+ T cell epitope nested within a CD4+ T cell epitope may be capable of generating a robust CTL response. The extended peptide (CD4+ T cell epitope) may be capable of inducing T helper mediated cytokine responses. Thus, inclusion of a flavivirus peptide comprising a CD8+ T cell epitope and a CD4+ T cell epitope in the vaccine composition may allow the vaccine composition to induce both cytotoxic and helper T cell responses.

The flavivirus peptide comprising a CD4+ T cell epitope may be attached to a nanoparticle. When the peptide comprising a CD4+ T cell epitope is a different peptide from the flavivirus peptide comprising one or more of the CD8+ T cell epitopes set out in SEQ ID NOs: 1 to 10, each peptide may be attached to the same nanoparticle or to a different nanoparticle. The nanoparticle may be a gold nanoparticle. Nanoparticles and attachment thereto are described below.

B Cell Epitopes

The vaccine composition of the invention may comprise a peptide comprising a B cell epitope. The vaccine composition may comprise two or more, such as three or more, four or more, five our more, ten or more, fifteen or more or twenty or more peptides comprising a B cell epitope. A B cell epitope is a peptide that is capable of recognition by a B cell receptor (BCR) present on a B cell. Preferably, recognition by the BCR results in activation and/or maturation of the B cell. B cell activation may lead to increased proliferation, and/or antibody production.

The B cell epitope may be a flavivirus CD4+ T cell epitope. That is, the B cell epitope may be a peptide that is expressed by one or more flaviviruses and that is capable of recognition by a B cell receptor (BCR) present on a B cell. Such peptides are known in the art.

The B cell epitope may be a linear epitope, i.e. an epitope that is defined by the primary amino acid sequence of a particular region of a filovirus protein. Alternatively, the epitope may be a conformational epitope, i.e. an epitope that is defined by the conformational structure of a native flavivirus protein. In this case, the epitope may be continuous (i.e. the components that interact with the antibody are situated next to each other sequentially on the protein) or discontinuous (i.e. the components that interact with the antibody are situated on disparate parts of the protein, which are brought close to each other in the folded native protein structure).

Typically, the B cell epitope is around 5 to 20 amino acids in length, such as 6 to 19, 7 to 18, 8 to 17, 9 to 16, 10 to 15, 11 to 14 or 12 to 13 amino acids in length.

Methods for identifying B cell epitopes are also known in the art. For instance, epitope mapping methods may be used to identify B cell epitopes. These methods include structural approaches, wherein the known or modelled structure of a protein is be used in an algorithm based approach to predict surface epitopes, and functional approaches, wherein the binding of whole proteins, protein fragments or peptides to an antibody can be quantitated e.g. using an Enzyme-Linked Immunosorbent Assay (ELISA). Competition mapping, antigen modification or protein fragmentation methods may also be used.

Nanoparticles

In the vaccine composition of the invention, the flavivirus peptide comprising one or more of the CD8+ T cell epitopes set out in SEQ ID NOs: 1 to 10 may be attached to a nanoparticle. Any other peptides further comprised in the vaccine composition may also be attached to a nanoparticle. Attachment to a nanoparticle, for example a gold nanoparticle, is beneficial.

As set out above and demonstrated in the Examples below, attachment of the peptide to a nanoparticle (such as a gold nanoparticle) reduces or eliminates the need to include a virus or an adjuvant in the vaccine composition. The nanoparticles may contain immune "danger signals" that help to effectively induce an immune response to the peptides. The nanoparticles may induce dendritic cell (DC) activation and maturation, required for a robust immune response. The nanoparticles may contain non-self components that improve uptake of the nanoparticles and thus the peptides by cells, such as antigen presenting cells. Attachment of a peptide to a nanoparticle may therefore enhance the ability of antigen presenting cells to stimulate virus-specific T and/or B cells. Attachment to a nanoparticle also facilitates delivery of the vaccine compositions via the subcutaneous, intradermal, transdermal and oral/buccal routes, providing flexibility in administration.

Nanoparticles are particles between 1 and 100 nanometers (nm) in size which can be used as a substrate for immobilising ligands. In the vaccine compositions of the invention, the nanoparticle may have a mean diameter of 1 to 100, 20 to 90, 30 to 80, 40 to 70 or 50 to 60 nm. Preferably, the nanoparticle has a mean diameter of 20 to 40 nm. A mean diameter of 20 to 40 nm facilitates uptake of the nanoparticle to the cytosol. The mean diameter can be measured using techniques well known in the art such as transmission electron microscopy.

Nanoparticles suitable for the delivery of antigen, such as a flavivirus peptide, are known in the art. Methods for the production of such nanoparticles are also known.

The nanoparticle may, for example, be a polymeric nanoparticle, an inorganic nanoparticle, a liposome, an immune stimulating complex (ISCOM), a virus-like particle (VLP), or a self-assembling protein. The nanoparticle is preferably a calcium phosphate nanoparticle, a silicon nanoparticle or a gold nanoparticle.

The nanoparticle may be a polymeric nanoparticle. The polymeric nanoparticle may comprise one or more synthetic polymers, such as poly(d,l-lactide-co-glycolide) (PLG), poly(d,l-lactic-coglycolic acid) (PLGA), poly(g-glutamic acid) (g-PGA)m poly(ethylene glycol) (PEG), or polystyrene. The polymeric nanoparticle may comprise one or more natural polymers such as a polysaccharide, for example pullulan, alginate, inulin, and chitosan. The use of a polymeric nanoparticle may be advantageous due to the properties of the polymers that may be include in the nanoparticle. For instance, the natural and synthetic polymers recited above may have good biocompatibility and biodegradability, a non-toxic nature and/or the ability to be manipulated into desired shapes and sizes. The polymeric nanoparticle may form a hydrogel nanoparticle. Hydrogel nanoparticles are a type of nano-sized hydrophilic three-dimensional polymer network. Hydrogel nanoparticles have favourable properties including flexible mesh size, large surface area for multivalent conjugation, high water content, and high loading capacity for antigens. Polymers such as Poly(L-lactic acid) (PLA), PLGA, PEG, and polysaccharides are particularly suitable for forming hydrogel nanoparticles.

The nanoparticle may be an inorganic nanoparticle. Typically, inorganic nanoparticles have a rigid structure and are non-biodegradable. However, the inorganic nanoparticle may be biodegradable. The inorganic nanoparticle may comprise a shell in which an antigen may be encapsulated. The inorganic nanoparticle may comprise a core to which an antigen may be covalently attached. The core may comprise a metal. For example, the core may comprise gold (Au), silver (Ag) or copper (Cu) atoms. The core may be formed of more than one type of atom. For instance, the core may comprise an alloy, such as an alloy of Au/Ag, Au/Cu, Au/Ag/Cu, Au/Pt, Au/Pd or Au/Ag/Cu/Pd. The core may comprise calcium phosphate (CaP). The core may comprise a semiconductor material, for example cadmium selenide.

Other exemplary inorganic nanoparticles include carbon nanoparticles and silica-based nanoparticles. Carbon nanoparticles are have good biocompatibility and can be synthesized into nanotubes and mesoporous spheres. Silica-based nanoparticles (SiNPs) are biocompatible and can be prepared with tunable structural parameters to suit their therapeutic application.

The nanoparticle may be a silicon nanoparticle, such as an elemental silicon nanoparticle. The nanoparticle may be mesoporous or have a honeycomb pore structure. Preferably, the nanoparticle is an elemental silicon particle having a honeycomb pore structure. Such nanoparticles are known in the art and offer tunable and controlled drug loading, targeting and release that can be tailored to almost any load, route of administration, target or release profile. For example, such nanoparticles may increase the bioavailability of their load, and/or improve the intestinal permeability and absorption of orally administered actives. The nanoparticles may have an exceptionally high loading capacity due to their porous structure and large surface area. The nanoparticles may release their load over days, weeks or months, depending on their physical properties. Since silicon is a naturally occurring element of the human body, the nanoparticles may elicit no response from the immune system. This is advantageous to the in vivo safety of the nanoparticles.

Any of the SiNPs described above may be biodegradable or non-biodegradable. A biodegradable SiNP may dissolve to orthosilic acid, the bioavailable form of silicon. Orthosilic acid has been shown to be beneficial for the health of bones, connective tissue, hair, and skin.

The nanoparticle may be a liposome. Liposomes are typically formed from biodegradable, non-toxic phospholipids and comprise a self-assembling phospholipid bilayer shell with an aqueous core. A liposome may be an unilameller vesicle comprising a single phospholipid bilayer, or a multilameller vesicle that comprises several concentric phospholipid shells separated by layers of water. As a consequence, liposomes can be tailored to incorporate either hydrophilic molecules into the aqueous core or hydrophobic molecules within the phospholipid bilayers. Liposomes may encapsulate antigen within the core for delivery. Liposomes may incorporate viral envelope glycoproteins to the shell to form virosomes. A number of liposome-based products are established in the art and are approved for human use.

The nanoparticle may be an immune-stimulating complex (ISCOM). ISCOMs are cage-like particles which are typically formed from colloidal saponin-containing micelles. ISCOMs may comprise cholesterol, phospholipid (such as phosphatidylethanolamine or phosphatidylcholine) and saponin (such as Quil A from the tree *Quillaia saponaria*). ISCOMs have traditionally been used to entrap viral envelope proteins, such as envelope proteins from herpes simplex virus type 1, hepatitis B, or influenza virus.

The nanoparticle may be a virus-like particle (VLP). VLPs are self-assembling nanoparticles that lack infectious nucleic acid, which are formed by self-assembly of biocompatible capsid protein. VLPs are typically about 20 to about 150 nm, such as about 20 to about 40 nm, about 30 to about 140 nm, about 40 to about 130 nm, about 50 to about 120 nm, about 60 to about 110 nm, about 70 to about 100 nm, or about 80 to about 90 nm in diameter. VLPs advantageously harness the power of evolved viral structure, which is naturally optimized for interaction with the immune system. The naturally-optimized nanoparticle size and repetitive structural order means that VLPs induce potent immune responses, even in the absence of adjuvant.

The nanoparticle may be a self-assembling protein. For instance, the nanoparticle may comprise ferritin. Ferritin is a protein that can self-assemble into nearly-spherical 10 nm structures. The nanoparticle may comprise major vault protein (MVP). Ninety-six units of MVP can self-assemble into a barrel-shaped vault nanoparticle, with a size of approximately 40 nm wide and 70 nm long.

The nanoparticle may be a calcium phosphate (CaP) nanoparticle. CaP nanoparticles may comprise a core comprising one or more (such as two or more, 10 or more, 20 or more, 50 or more, 100 or more, 200 or more, or 500 or more) molecules of CaP. CaP nanoparticles and methods for their production are known in the art. For instance, a stable nano-suspension of CAP nanoparticles may be generated by mixing inorganic salt solutions of calcium and phosphates in pre-determined ratios under constant mixing.

The CaP nanoparticle may have an average particle size of about 80 to about 100 nm, such as about 82 to about 98 nm, about 84 to about 96 nm, about 86 to about 94 nm, or about 88 to about 92 nm. This particle size may produce a better performance in terms of immune cell uptake and immune response than other, larger particle sizes. The particle size may be stable (i.e. show no significant change), for instance when measured over a period of 1 month, 2 months, 3 months, 6 months, 12 months, 18 months, 24 months, 36 months or 48 months.

CaP nanoparticles can be co-formulated with one or multiple antigens either adsorbed on the surface of the nanoparticle or co-precipitated with CaP during particle synthesis. For example, a peptide, such as a flavivirus peptide, may be attached to the CaP nanoparticle by dissolving the peptide in DMSO (for example at a concentration of about 10 mg/ml), adding to a suspension of CaP nanoparticles together with N-acetylglucosamine (GlcNAc) (for example at 0.093 mol/L and ultra-pure water, and mixing at room temperature for a period of about 4 hours (for example, 1 hour, 2 hours, 3 hours, 5 hours, 6 hours, 7 hours, 8 hours, 9 hours or 10 hours).

The vaccine composition may comprise about 0.15 to about 0.8%, such as 0.2 to about 0.75%, 0.25 to about 0.7%, 0.3 to about 0.6%, 0.35 to about 0.65%, 0.4 to about 0.6%, or 0.45 to about 0.55%, CaP nanoparticles. Preferably the vaccine composition comprises about 0.3% CaP nanoparticles.

CaP nanoparticles have a high degree of biocompatibility due to their chemical similarity to human hard tissues such as bone and teeth. Advantageously, therefore, CaP nanoparticles are non-toxic when used for therapeutic applications. CaP nanoparticles are safe for administration via intramuscular, subcutaneous, oral, or inhalation routes. CaP nanoparticles are also simple to synthesise commercially. Furthermore, CaP nanoparticles may be associated with slow release of antigen, which may enhance the induction of an immune response to a peptide attached to the nanoparticle. CaP nanoparticles may be used both as an adjuvant, and as a drug delivery vehicle.

The nanoparticle may be a gold nanoparticle. Gold nanoparticles are known in the art and are described in particular in WO 2002/32404, WO 2006/037979, WO 2007/122388, WO 2007/015105 and WO 2013/034726. The gold nanoparticle attached to each peptide may be a gold nanoparticle described in any of WO 2002/32404, WO 2006/037979, WO 2007/122388, WO 2007/015105 and WO 2013/034726.

Gold nanoparticles comprise a core comprising a gold (Au) atom. The core may further comprise one or more Fe, Cu or Gd atoms. The core may be formed from a gold alloy, such as Au/Fe, Au/Cu, Au/Gd, Au/Fe/Cu, Au/Fe/Gd or Au/Fe/Cu/Gd. The total number of atoms in the core may be 100 to 500 atoms, such as 150 to 450, 200 to 400 or 250 to 350 atoms. The gold nanoparticle may have a mean diameter of 1 to 100, 20 to 90, 30 to 80, 40 to 70 or 50 to 60 nm. Preferably, the gold nanoparticle has a mean diameter of 20 to 40 nm.

The nanoparticle may comprise a surface coated with alpha-galactose and/or beta-GlcNHAc. For instance, the nanoparticle may comprise a surface passivated with alpha-galactose and/or beta-GlcNHAc. In this case, the nanoparticle may, for example, be a nanoparticle which comprises a core including metal and/or semiconductor atoms. For instance, the nanoparticle may be a gold nanoparticle. Beta-GlcNHAc is a bacterial pathogen-associated-molecular pattern (PAMP), which is capable of activating antigen-presenting cells. In this way, a nanoparticle comprising a surface coated or passivated with Beta-GlcNHAc may non-specifically stimulate an immune response. Attachment of the flavivirus peptide comprising one or more of the CD8+ T cell epitopes set out in SEQ ID NOs: 1 to 10 to such a nanoparticle may therefore improve the immune response elicited by administration of the vaccine composition of the invention to an individual.

One or more ligands other than the peptide may be linked to the nanoparticle, which may be any of the types of nanoparticle described above. The ligands may form a "corona", a layer or coating which may partially or completely cover the surface of the core. The corona may be considered to be an organic layer that surrounds or partially surrounds the nanoparticle core. The corona may provide or participate in passivating the core of the nanoparticle. Thus, in certain cases the corona may be a sufficiently complete coating layer to stabilise the core. The corona may facilitate solubility, such as water solubility, of the nanoparticles of the present invention.

The nanoparticle may comprise at least 10, at least 20, at least 30, at least 40 or at least 50 ligands. The ligands may include one or more peptides, protein domains, nucleic acid molecules, lipidic groups, carbohydrate groups, anionic groups, or cationic groups, glycolipids and/or glycoproteins. The carbohydrate group may be a polysaccharide, an oligosaccharide or a monosaccharide group (e.g. glucose). One or more of the ligands may be a non-self component, that renders the nanoparticle more likely to be taken up by antigen presenting cells due to its similarity to a pathogenic component. For instance, one or more ligands may comprise a carbohydrate moiety (such as a bacterial carbohydrate moiety), a surfactant moiety and/or a glutathione moiety. Exemplary ligands include glucose, N-acetylglucosamine (GlcNAc), glutathione, 2'-thioethyl-β-D-glucopyranoside and 2'-thioethyl-D-glucopyranoside. Preferred ligands include glycoconjugates, which form glyconanoparticles Linkage of the ligands to the core may be facilitated by a linker. The linker may comprise a thiol group, an alkyl group, a glycol group or a peptide group. For instance, the linker may comprise C2-C15 alkyl and/or C2-C15 glycol. The linker may comprise a sulphur-containing group, amino-containing group, phosphate-containing group or oxygen-containing group that is capable of covalent attachment to the core. Alternatively, the ligands may be directly linked to the core, for example via a sulphur-containing group, amino-containing group, phosphate-containing group or oxygen-containing group comprised in the ligand.

Attachment to Nanoparticles

The peptide may be attached at its N-terminus to the nanoparticle. Typically, the peptide is attached to the core of the nanoparticle, but attachment to the corona or a ligand may also be possible.

The peptide may be directly attached to the nanoparticle, for example by covalent bonding of an atom in a sulphur-containing group, amino-containing group, phosphate-containing group or oxygen-containing group in the peptide to an atom in the nanoparticle or its core.

A linker may be used to link the peptide to the nanoparticle. The linker may comprise a sulphur-containing group, amino-containing group, phosphate-containing group or oxygen-containing group that is capable of covalent attachment to an atom in the core. For example, the linker may comprise a thiol group, an alkyl group, a glycol group or a peptide group.

The linker may comprise a peptide portion and a non-peptide portion. The peptide portion may comprise the sequence $X_1X_2Z_1$, wherein $X_1$ is an amino acid selected from A and G; $X_2$ is an amino acid selected from A and G; and $Z_1$ is an amino acid selected from Y and F. The peptide portion may comprise the sequence AAY or FLAAY. The peptide portion of the linker may be linked to the N-terminus of the peptide. The non-peptide portion of the linker may comprise a C2-C15 alkyl and/a C2-C15 glycol, for example a thioethyl group or a thiopropyl group.

The linker may be (i) HS—$(CH_2)_2$—CONH-AAY; (ii) HS—$(CH_2)_2$—CONH-LAAY; (iii) HS—$(CH_2)_3$—CONH-AAY; (iv) HS—$(CH_2)_3$—CONH-FLAAY; (v) HS—$(CH_2)_{10}$—$(CH_2OCH_2)_7$—CONH-AAY; and (vi) HS—$(CH_2)_{10}$—$(CH_2OCH_2)_7$—CONH-FLAAY. In this case, the thiol group of the non-peptide portion of the linker links the linker to the core.

Other suitable linkers for attaching a peptide to a nanoparticle are known in the art, and may be readily identified and implemented by the skilled person.

As explained above, the vaccine composition may comprise multiple flavivirus peptides each comprising one or more of the CD8+ T cell epitopes set out in SEQ ID NOs: 1 to 9. The vaccine composition may comprise one or more additional peptides each comprising an epitope, such as a CD4+ T cell epitope, a B cell epitope, or a CD8+ T cell epitope other than the CD8+ T cell epitopes set out in SEQ ID NOs: 1 to 9. Thus, the vaccine composition may comprise more than one peptide.

When the vaccine composition comprises more than one peptide, two or more (such as three or more, four or more, five or more, ten or more, or twenty or more) of the peptides may be attached to the same nanoparticle. Two or more (such as three or more, four or more, five or more, ten or more, or twenty or more) of the peptides may each be attached to different nanoparticle. The nanoparticles to which the peptides are attached may though be the same type of nanoparticle. For instance, each peptide may be attached to a gold nanoparticle. Each peptide may be attached to a CaP nanoparticle. The nanoparticle to which the peptides are attached may be a different type of nanoparticle. For instance, one peptide may be attached to a gold nanoparticle, and another peptide may be attached to a CaP nanoparticle.

Medicaments, Methods and Therapeutic Use

The invention provides a method of preventing or treating a flavivirus infection, comprising administering the vaccine composition of the inventions to an individual infected with, or at risk of being infected with, a flavivirus. The invention also provides a vaccine composition of the invention for use in a method of preventing or treating a flavivirus infection in an individual.

The flavivirus infection may be, for example, a Zika virus infection, a Dengue virus infection, a West Nile virus infection, a yellow fever virus infection, a St. Louis encephalitis virus infection, a Japanese encephalitis virus infection, a Murray Valley encephalitis virus infection, a Tick-borne encephalitis virus infection, a Kunjin encephalitis virus infection, a Rocio encephalitis virus infection, a Russian Spring Summer encephalitis virus infection, Negeishi virus infection, a Kyasanur Forest infection, a Omsk Hemorrhagic Fever virus infection, a Powassan virus infection, a Louping Ill virus infection, a Rio Bravo virus infection, a Tyuleniy virus infection, a Ntaya virus infection or a Modoc virus infection. The Zika virus infection may, for example, be African Zika Virus infection or Asian Zika Virus infection. The Dengue virus may, for example, be DENV-1 infection, DENV-2 infection, DENV-3 infection or DENV-4 infection.

The vaccine composition may be provided as a pharmaceutical composition. The pharmaceutical composition preferably comprises a pharmaceutically acceptable carrier or diluent. The pharmaceutical composition may be formulated using any suitable method. Formulation of cells with standard pharmaceutically acceptable carriers and/or excipients may be carried out using routine methods in the pharmaceutical art. The exact nature of a formulation will depend upon several factors including the cells to be administered and the desired route of administration. Suitable types of formulation are fully described in Remington's Pharmaceutical Sciences, 19th Edition, Mack Publishing Company, Eastern Pennsylvania, USA.

The vaccine composition or pharmaceutical composition may be administered by any route. Suitable routes include, but are not limited to, the intravenous, intramuscular, intraperitoneal, subcutaneous, intradermal, transdermal and oral/buccal routes.

Compositions may be prepared together with a physiologically acceptable carrier or diluent. Typically, such compositions are prepared as liquid suspensions of peptides and/or peptide-linked nanoparticles. The peptides and/or peptide-linked nanoparticles may be mixed with an excipient which is pharmaceutically acceptable and compatible with the active ingredient. Suitable excipients are, for example, water, saline, dextrose, glycerol, of the like and combinations thereof.

In addition, if desired, the pharmaceutical compositions may contain minor amounts of auxiliary substances such as wetting or emulsifying agents, and/or pH buffering agents.

The peptides or peptide-linked nanoparticles are administered in a manner compatible with the dosage formulation and in such amount will be therapeutically effective. The quantity to be administered depends on the subject to be treated, the disease to be treated, and the capacity of the subject's immune system. Precise amounts of nanoparticles required to be administered may depend on the judgement of the practitioner and may be peculiar to each subject.

Any suitable number of peptides or peptide-linked nanoparticles may be administered to a subject. For example, at least, or about, $0.2 \times 10^6$, $0.25 \times 10^6$, $0.5 \times 10^6$, $1.5 \times 10^6$, $4.0 \times 10^6$ or $5.0 \times 10^6$ peptides or peptide-linked nanoparticles per kg of patient may administered. For example, at least, or about, $10^5$, $10^6$, $10^7$, $10^8$, $10^9$ peptides or peptide-linked nanoparticles may be administered. As a guide, the number of peptides or peptide-linked nanoparticles to be administered may be from $10^5$ to $10^9$, preferably from $10^6$ to $10^8$.

It is to be understood that different applications of the disclosed products and methods may be tailored to the specific needs in the art. It is also to be understood that the terminology used herein is for the purpose of describing particular embodiments of the invention only, and is not intended to be limiting.

In addition, as used in this specification and the appended claims, the singular forms "a", "an", and "the" include plural referents unless the content clearly dictates otherwise. Thus, for example, reference to "a peptide" includes "peptides", reference to "a nanoparticle" includes two or more such nanoparticles, and the like.

All publications, patents and patent applications cited herein, whether supra or infra, are hereby incorporated by reference in their entirety.

The following Examples illustrate the invention.

Example 1—Identification of CD8+ T Cell Epitopes

Cell Lines

HepG2 hepatoma cells were obtained from ATCC and maintained in DMEM:F12 (Mediatech, Manassas, VA). Culture medium was supplemented with 10% fetal bovine serum, L-glutamine (300 mg/mL), non-essential amino acids (lx concentration), 0.5 mM sodium pyruvate, penicillin and streptomycin (1× concentration, supplements were purchased from Mediatech) [complete medium]. Cells were maintained at 37° C. in a humidified incubator with 5% CO2.

Preparation of Samples for MHC Peptide Analysis

HepG2 cells were grown to about 1E9 cells. These cells were then infected with Zika virus or Dengue virus respectively at five MOI. After a 1 hr pulse, virus was washed away, and cells were incubated for 72 hrs at 37° C. At this point, cells were harvested and processed for MHC peptide analysis.

Isolation, Purification and Fractionation of MHC Class I Bound Peptides

Infected cells were lysed by homogenization and freeze/thawed in buffer containing 1.0% NP40. The lysates were cleared by centrifugation at 2000 rpm for 30 minutes to remove the cell debris. MHC/peptide complexes were isolated by immunoaffinity chromatography using W6/32 antibody (monoclonal antibody recognizing pan MHC class I molecule) coated protein A/G beads (UltraLink Immobilized Protein A/G, Pierce, Rockford, IL). 400 µl Protein A/G beads were washed with low pH buffer followed by PBS rinses. The beads were then incubated with 0.5 mg of the antibody at room temperature for 2 hours. Labelled beads were washed three times to remove unbound antibodies, and antibody-coated beads were added to the prepared cell lysate. After a two-hour incubation at room temperature with continuous rocking, the beads were separated from the lysate by centrifuging at 1000 rpm for 5 minutes. The bound MHC complexes were eluted from the beads by the addition of 0.1% Trifluoroacetic acid, (TFA), pH 1.5. Next, the eluate was heated at 85° C. for 15 min to dissociate the bound peptides from the MHC molecules. After the solution was cooled to room temperature, peptides were separated from the antibody by centrifugation using Amicon Ultra-3 kDa molecular mass cutoff membrane filters (Millipore). The filtrate was concentrated using vacuum centrifugation and reconstituted to a final volume of 100 µL. The purified peptide mixture was fractionated using C-18 reversed phase (RP) column (4.6 mm diameter×150 mm length) using an offline ultimate 3000 HPLC (Dionex, Sunnyvale, CA). Mobile phase A was 2% acetonitrile (ACN) and 0.1% formic acid (FA) in water, while mobile phase B was 0.1% FA and 90% ACN in water. Peptides were then eluted from the column with an 80 min linear gradient from 5 to 80% buffer B at a flow rate of 200 µL/min. A total of 35 fractions were collected and dried to 6 µL under vacuum for LC/MS/MS analysis.

Mass Spectrometry Analysis

Mass spectrometry experiments were carried out using LTQ (Thermo) and Orbitrap instruments interfaced with nano ultimate HPLC (Dionex). RP-HPLC purified peptide fractions were injected individually into the LC-MS/MS system to identify the sequences of the peptides. As a part of the on-line sample clean-up step, the peptides were first concentrated using a 300 µm ID×5 mmC18 RP trap column (Dionex, Sunnyvale CA) and then separated using a 75 µm ID×15 cm C18 RP analytical column (Dionex, Sunnyvale CA), equilibrated in 4% ACN/0.1% FA at 250 nL/min flow rate. Mobile phase A was 2% ACN and 0.1% FA in water, while mobile phase B was 0.1% FA and 90% ACN in water. Peptides were separated with a gradient of 4% to 50% B in 60 min and 50% to 80% in 90 min and eluted directly into the mass spectrometer. The mass range in MS mode was 350 Da to 1500 Da and in MS/MS mode it was set as 100 Da to 1500 Da. The peptides were analyzed using a Data-Dependent method. The acquired spectra data were searched against Dengue (DV 1-4 serotypes) protein database using Proteome Discoverer (Thermo) to interpret data and derive peptide sequences.

Peptide Validation by Synthetic Peptides

Synthetic peptides for validating the peptides identified in this study were obtained from Genscript Corporation (Piscataway, NJ). The synthetic peptides were then subjected to LC-MS/MS analysis under identical experimental conditions as described above and their sequences were confirmed based on their MS/MS data. Candidate peptide sequences were confirmed by comparison of their MS/MS spectra with that of their synthetic analogs.

Results

The flavivirus peptides identified using the method set out above are shown in Table 2.

TABLE 2

| Notation | Sequence | Protein ID | HLA affinity | Origin | 100% sequence homology with . . . |
|---|---|---|---|---|---|
| P1 | PMAAVGLLIVS | NS2B | A2/A24 | Zika infected cells | Zika virus |
| P2 | AILEENGVQ | NS4B | A2 | Zika infected cells | Zika virus |
|  | SPRRLAAAV | NS1 | B7 | Zika infected cells | Zika virus, Dengue virus |
|  | DPAVIGTAVK | NS1 | B7 | Zika infected cells | Zika virus |
| P3 | WVTDHSGKTV | NS3 | A2 | Dengue infected cells | Zika virus, West Nile virus, Dengue virus |

TABLE 2-continued

| Notation | Sequence | Protein ID | HLA affinity | Origin | 100% sequence homology with . . . |
|---|---|---|---|---|---|
| | PFGDSYIVIGVGE | Envelope | A24 | Zika infected cells | Zika virus, |
| | DIGAVALDYPA | NS3 | A24 | Zika infected cells | DENV- 4 |
| P4 | LLGLITANEL | Peptike 2k | A2/A24 | Zika infected cells | Zika virus |
| P5 | IMLLGLLGTV | NS4 | A2 | Zika infected cells | Zika virus |
| | LMRNKGIGK | NS4A | A3 | Dengue infected cells | Zika virus |

Example 2

Methods

Epitope-specific CTLs were generated using peripheral blood mononuclear cells from healthy (naive) human HLA-A2+ donor. First, DCs were generated from an adherent population of PBMCs cultured in GM-CSF- and IL-4-containing medium. DCs obtained by this method (immature DCs) were pulsed with peptides (P1 to P5, individually) or nanoparticle-conjugate peptides (P1 to P5, individually). Both groups were supplemented with microglobulin. CD8+ T-cells were co-cultured with DCs at a ratio of 20:1 CD8+ T-cells to DCs in complete RPMI supplemented with 10% FBS and recombinant human IL-7 in 24 well plates. After three to four rounds of restimulation, cultures were analysed for CTL response.

Activated T-cells generated in accordance with this method were tested for cytotoxic activity against flavivirus peptide-loaded T2 cells, and flavivirus-infected HepG2 cells as targets in the following assays: production of IFN-γ and granzyme-B by ELISpot; cytokine secretion by MAGPIX assay; CD107a co-expression by flow cytometry.

Stimulation of CTL Responses In Vitro

Peripheral blood mononuclear cells (PBMCs) from a healthy (naive) human HLA-A2+ donor were stimulated with peptides P1 to P5 (individually) in a cytokine cocktail to induce an antigen specific CTL response. The HLA-A2+ PBMCs were stimulated with pooled free peptides (FPs) for a total of four stimulations at varying peptide loads.

These stimulated PBMCs were then assayed by co-culturing with uninfected, infected, or peptide loaded targets for antigen specific response. TAP-deficient cells (T2) were used for peptide loading, and blank T2 cells were used as a control. Activated PBMCs were assayed for both interferon gamma (IFNγ) and CD107a degranulation markers by flow cytometry.

Results are shown in FIGS. 1 to 4.

Example 3

Figure 5:
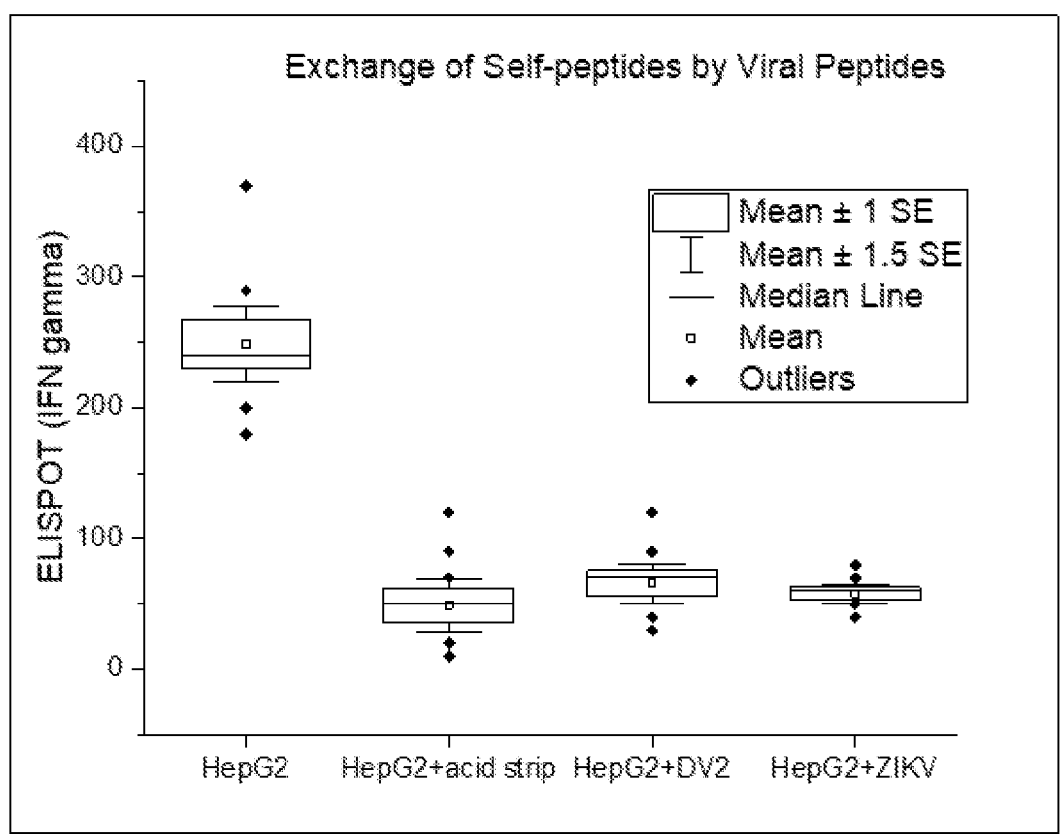
FIG. 5: Transgenic A2 mice were immunized with 200 ng of NP-Dengue peptides. The spleen cells were isolated and then exposed to either Zika or Dengue infected cells.
Figure 6:
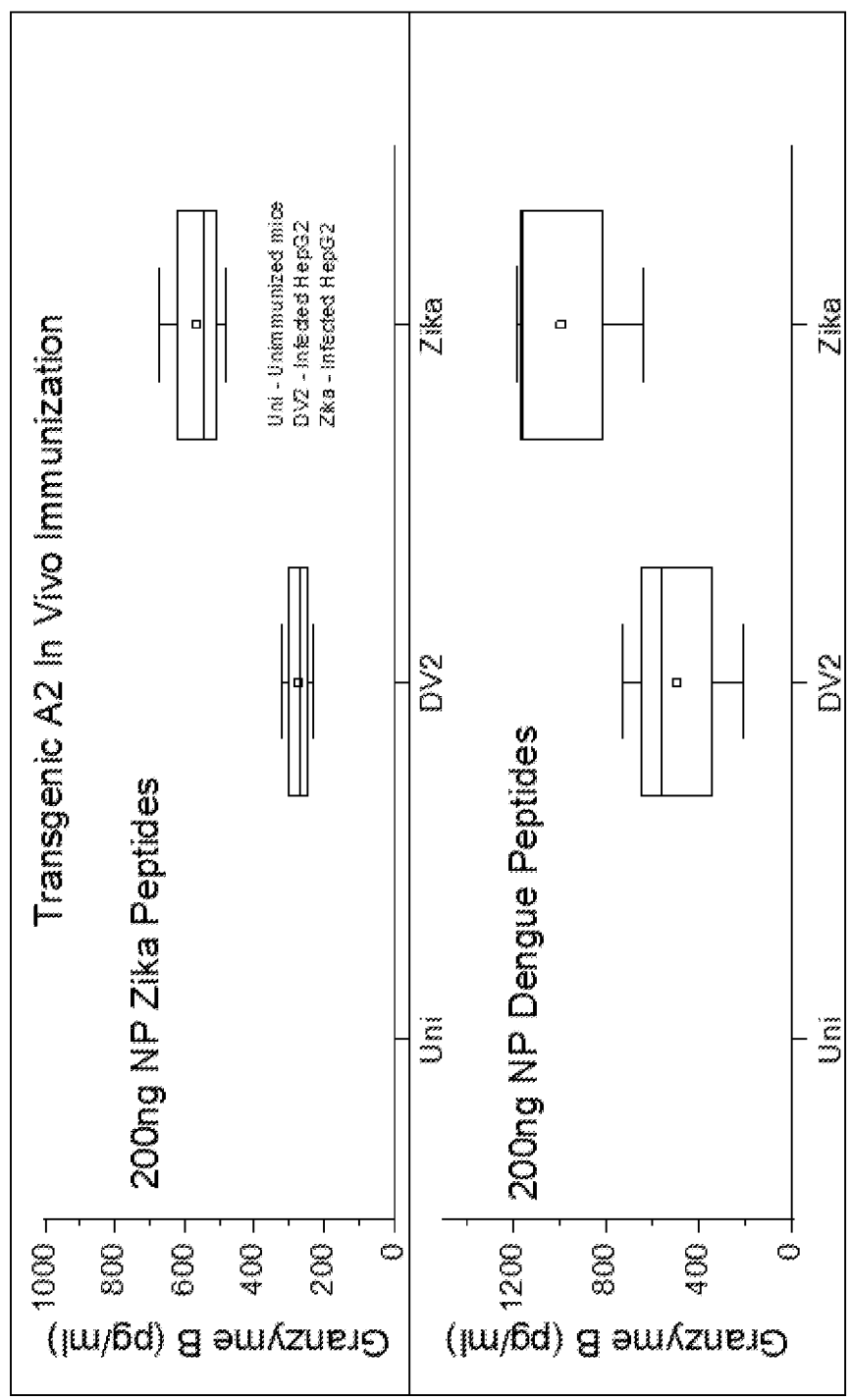
FIG. 6: Transgenic A2 mice were immunized with 200 ng of NP-Dengue peptides. The spleen cells were isolated and then exposed to either Zika or Dengue infected cells. Infection of the HepG2 cells with flaviviruses displaces the self-peptides and results in exposure of the viral derived peptides on the cell surface as shown in FIG. 6.

Transgenic A2 mice were immunized with 200 ng of NP-Dengue peptides. The spleen cells were isolated and then exposed to either Zika or Dengue infected cells. FIG. 5 shows that HepG2 target cells contain peptide class I targets that are able to simulate spleen cells from transgenic A2 mice. Acid stripping of the peptides makes the cells non-responsive. Similarly, infection of the HepG2 cells with flaviviruses displaces the self-peptides and results in exposure of the viral derived peptides on the cell surface as shown in FIG. 6. FIG. 6 shows that spleen cells from unimmunized mice do not respond to dengue or zika infected cells. In contrast A2 mice immunized with NP-Dengue or NP-Zika peptides are able to kill both Dengue or Zika infected HepG2 cells.

Example 4

Stimulation of CTL Responses In Vitro

Peripheral blood mononuclear cells (PBMCs) from a healthy (naive) human HLA-A24+ donor are stimulated with peptides P1 to P5 (individually) in a cytokine cocktail to induce an antigen specific CTL response. The HLA-A24+ PBMCs are stimulated with pooled free peptides (FPs) for a total of four stimulations at varying peptide loads.

These stimulated PBMCs are then assayed by co-culturing with uninfected, infected, or peptide loaded targets for antigen specific response. TAP-deficient cells (T2) are used for peptide loading, and blank T2 cells are used as a control. Activated PBMCs are assayed for both interferon gamma (IFNγ) and CD107a degranulation markers by flow cytometry.

Dextramer Studies

Dextramer reagents are fluorescently labelled and are used to detect antigen specific T-cells in cell suspensions and solid tissue samples. MHC dextramers are added to PBMCs or splenocytes. An optimal amount of anti-CD8 antibody conjugated with a relevant fluorochrome is then added. Additional antibodies (e.g. anti-CD3 or anti-CD4 antibodies) conjugated with other relevant fluorochromes may also be added at this step. Cells are then analysed using a flow cytometer.

In Vivo CTL Studies

HLA A2/A24 transgenic mice (5-6 mice per group) are immunised with free synthetic peptide or nanoparticle-peptide conjugates mixed with and without montanide-51 adjuvant three times at 2-week intervals by subcutaneous and intra-dermal routes of administration. Spleen and draining lymph nodes are collected 7 days after the final boost for CTL analysis. Single cell suspensions are prepared from the lymphoid organs and cells are stimulated with peptide antigens in culture for 7 days. The reactivated T-cells are assayed for epitope specific CTL responses using flavivirus peptide-loaded T2 cells and flavivirus-infected HepG2 cells as targets in the following assays: production of IFN-γ and granzyme-B by ELISpot; cytokine secretion by MAGPIX assay; CD107a co-expression by flow cytometry.

Adoptive Transfer Experiments

Adoptive transfer experiments are performed to investigate whether peptide-specific CTL generated in HLA-A2 transgenic mice have cytotoxic effect against flavivirus infected cells in vivo in SCID-Beige mice. Infected liver tumour suspension is injected sc or iv into SCID Beige mice, followed by single or multiple adoptive transfer of peptide specific CTL generated in transgenic A2 mice against peptide-NP constructs. Appropriate controls are used. Survival of mice is monitored.

The invention claimed is:

1. A vaccine composition comprising a flavivirus peptide comprising one or more of the CD8+ T cell epitopes selected from SEQ ID NOs: 6 and 8 wherein the flavivirus peptide is attached to a gold nanoparticle, a calcium phosphate nanoparticle, or a silicon nanoparticle, and wherein the flavivirus peptide is no more than 15 amino acids in length.

2. The vaccine composition of claim 1, wherein the gold nanoparticle is coated with alpha-galactose and/or beta-N-acetylglucosamine (beta-GlcNAc).

3. The vaccine composition of claim 1, wherein the flavivirus peptide is attached to the nanoparticle via a linker.

4. The vaccine composition of claim 1, further comprising one or more additional flavivirus peptides wherein each additional flavivirus peptide comprises a different CD8+ T cell epitope.

5. The vaccine composition of claim 4, wherein the additional flavivirus peptides are selected from SEQ ID NOs: 6 and 8.

6. The vaccine composition of claim 1, further comprising at least one flavivirus peptide comprising a CD8+ T cell epitope, wherein the CD8+ T cell epitopes each interact with a different HLA supertype.

7. The vaccine composition of claim 1, wherein the at least one flavivirus peptide comprises a CD8+ T cell epitope that interacts with at least two different HLA supertypes.

8. The vaccine composition of claim 6, wherein the different HLA supertypes are selected from HLA-A1, HLA-A2, HLA-A3, HLA-A24, HLA-B7, HLA-B8, HLA-B27, HLA-B44, HLA-B58 and HLA-B62.

9. The vaccine composition of claim 8, wherein the different HLA supertypes are HLA-A2 and HLA-A24.

10. The vaccine composition of claim 1, wherein the CD8+ T cell epitope selected from SEQ ID NOs: 6 and 8 is conserved between flaviviruses.

11. The vaccine composition of claim 1, wherein the CD8+ T cell epitope selected from SEQ ID NOs: 6 and 8 is conserved between Zika viruses, West Nile viruses and/or Dengue viruses.

12. The vaccine composition of claim 1, comprising at least one flavivirus peptide that comprises a CD4+ T cell epitope.

13. The vaccine composition of claim 12, wherein the CD4+ T cell epitope interacts with all HLA class II types.

14. The vaccine composition of claim 12, wherein the CD4+ T cell epitope is selected from SEQ ID NO: 11 and 12.

15. A method of preventing or treating a flavivirus infection, comprising administering the vaccine composition of claim 1 to an individual infected with, or at risk of being infected with, a flavivirus.

16. The method of claim 15, wherein the flavivirus infection is a Zika virus infection, West Nile virus infection and/or Dengue virus infection.

17. The method of claim 16, wherein:
(a) the Zika virus infection is an African Zika virus or an Asian Zika virus infection; and/or
(b) the Dengue virus infection is a Dengue virus 1, Dengue virus 2, Dengue virus 3, or Dengue virus 4 infection.

18. A vaccine composition comprising a flavivirus peptide comprising one or more of the CD8+ T cell epitopes selected from SEQ ID NOs: 6 and 8, wherein the flavivirus peptide is attached to a gold nanoparticle, a calcium phosphate nanoparticle, or a silicon nanoparticle, and wherein the flavivirus peptide is 13 to about 20 amino acids in length.

* * * * *

SEQUENCE LISTING

```
<160> NUMBER OF SEQ ID NOS: 14

<210> SEQ ID NO 1
<211> LENGTH: 11
<212> TYPE: PRT
<213> ORGANISM: Zika virus

<400> SEQUENCE: 1

Pro Met Ala Ala Val Gly Leu Leu Ile Val Ser
1               5                   10

<210> SEQ ID NO 2
<211> LENGTH: 9
<212> TYPE: PRT
<213> ORGANISM: Zika virus

<400> SEQUENCE: 2

Ala Ile Leu Glu Glu Asn Gly Val Gln
1               5

<210> SEQ ID NO 3
<211> LENGTH: 9
<212> TYPE: PRT
<213> ORGANISM: Zika virus

<400> SEQUENCE: 3

Ser Pro Arg Arg Leu Ala Ala Ala Val
1               5

<210> SEQ ID NO 4
<211> LENGTH: 10
<212> TYPE: PRT
<213> ORGANISM: Zika virus

<400> SEQUENCE: 4

Asp Pro Ala Val Ile Gly Thr Ala Val Lys
1               5                   10

<210> SEQ ID NO 5
<211> LENGTH: 10
<212> TYPE: PRT
<213> ORGANISM: Dengue virus

<400> SEQUENCE: 5

Trp Val Thr Asp His Ser Gly Lys Thr Val
1               5                   10

<210> SEQ ID NO 6
<211> LENGTH: 13
<212> TYPE: PRT
<213> ORGANISM: Zika virus

<400> SEQUENCE: 6

Pro Phe Gly Asp Ser Tyr Ile Val Ile Gly Val Gly Glu
1               5                   10

<210> SEQ ID NO 7
<211> LENGTH: 11
<212> TYPE: PRT
<213> ORGANISM: Zika virus
```

```
<400> SEQUENCE: 7

Asp Ile Gly Ala Val Ala Leu Asp Tyr Pro Ala
1               5                  10

<210> SEQ ID NO 8
<211> LENGTH: 10
<212> TYPE: PRT
<213> ORGANISM: Zika virus

<400> SEQUENCE: 8

Leu Leu Gly Leu Ile Thr Ala Asn Glu Leu
1               5                  10

<210> SEQ ID NO 9
<211> LENGTH: 10
<212> TYPE: PRT
<213> ORGANISM: Zika virus

<400> SEQUENCE: 9

Ile Met Leu Leu Gly Leu Leu Gly Thr Val
1               5                  10

<210> SEQ ID NO 10
<211> LENGTH: 9
<212> TYPE: PRT
<213> ORGANISM: Dengue virus

<400> SEQUENCE: 10

Leu Met Arg Asn Lys Gly Ile Gly Lys
1               5

<210> SEQ ID NO 11
<211> LENGTH: 18
<212> TYPE: PRT
<213> ORGANISM: Clostridium tetani

<400> SEQUENCE: 11

Phe Lys Leu Gln Thr Met Val Lys Leu Phe Asn Arg Ile Lys Asn Asn
1               5                  10                  15

Val Ala

<210> SEQ ID NO 12
<211> LENGTH: 19
<212> TYPE: PRT
<213> ORGANISM: Clostridium tetani

<400> SEQUENCE: 12

Leu Gln Thr Met Val Lys Leu Phe Asn Arg Ile Lys Asn Asn Val Ala
1               5                  10                  15

Gly Gly Cys

<210> SEQ ID NO 13
<211> LENGTH: 4
<212> TYPE: PRT
<213> ORGANISM: Artificial Sequence
<220> FEATURE:
<223> OTHER INFORMATION: Linker sequence

<400> SEQUENCE: 13

Leu Ala Ala Tyr
1

<210> SEQ ID NO 14
```

```
<211> LENGTH: 5
<212> TYPE: PRT
<213> ORGANISM: Artificial Sequence
<220> FEATURE:
<223> OTHER INFORMATION: Linker sequence

<400> SEQUENCE: 14

Phe Leu Ala Ala Tyr
1               5
```